United States Patent

Knothe et al.

[11] Patent Number: 5,888,228
[45] Date of Patent: Mar. 30, 1999

[54] INTERVERTEBRAL IMPLANT WITH CAGE AND ROTATING ELEMENT

[75] Inventors: Inga Knothe, Biel; Alfred Benoit, Lengnau, both of Switzerland

[73] Assignee: Synthes (U.S.A.), Paoli, Pa.

[21] Appl. No.: 11,014

[22] PCT Filed: Oct. 20, 1995

[86] PCT No.: PCT/CH95/00243

§ 371 Date: Feb. 2, 1998

§ 102(e) Date: Feb. 2, 1998

[87] PCT Pub. No.: WO97/15246

PCT Pub. Date: May 1, 1997

[51] Int. Cl.$^6$ .................................................. A61F 2/44
[52] U.S. Cl. .................................................. 623/17
[58] Field of Search .......................... 623/17, 16; 606/61

[56] References Cited

U.S. PATENT DOCUMENTS

| | | | |
|---|---|---|---|
| 5,055,104 | 10/1991 | Ray | 606/61 |
| 5,192,327 | 3/1993 | Brantigan | 623/17 |
| 5,423,816 | 6/1995 | Lin | 606/61 |
| 5,683,463 | 11/1997 | Godefroy et al. | 623/17 |
| 5,766,253 | 6/1998 | Brosnahan, III | 623/17 |
| 5,782,919 | 7/1998 | Zdeblick et al. | 623/17 |

FOREIGN PATENT DOCUMENTS

| | | |
|---|---|---|
| WO89/09035 | 10/1989 | WIPO . |
| WO91/06261 | 5/1991 | WIPO . |
| WO94/17759 | 8/1994 | WIPO . |

*Primary Examiner*—David H. Willse
*Assistant Examiner*—Suzette J. Jackson
*Attorney, Agent, or Firm*—Pennie & Edmonds LLP

[57] ABSTRACT

The intervertebral implant comprises a frame-type cage (1) which is open at its top and base faces (11 and 12 respectively) with two lateral faces (13, 14), a front wall (15) and a rear wall (16). A rotating element (2) is mounted in the cage (1) so as to be capable of rotation. The outer surface of the rotating element (2) is provided with a helical structure (21). The helical structure (21) protrudes beyond the cover and base faces (11, 12) outside the confines of the cage (1). The front wall (15) has an aperture (17) for the introduction of a drive tool with which the rotating element (2) in the cage (1) can be made to rotate.

12 Claims, 2 Drawing Sheets

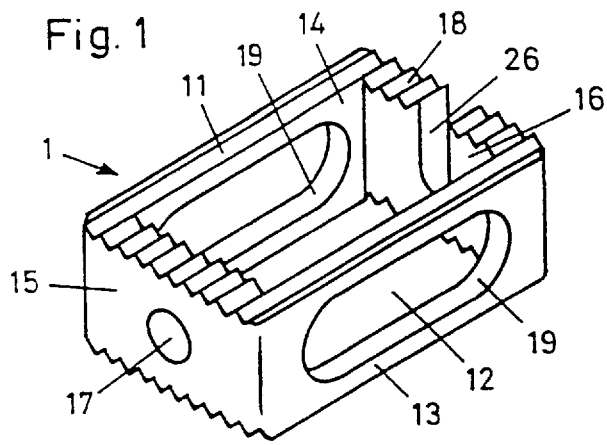
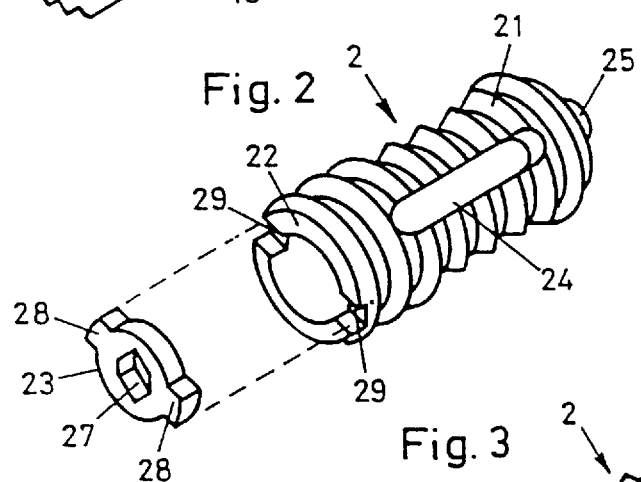
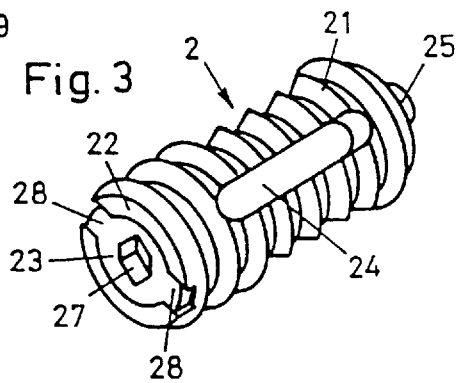
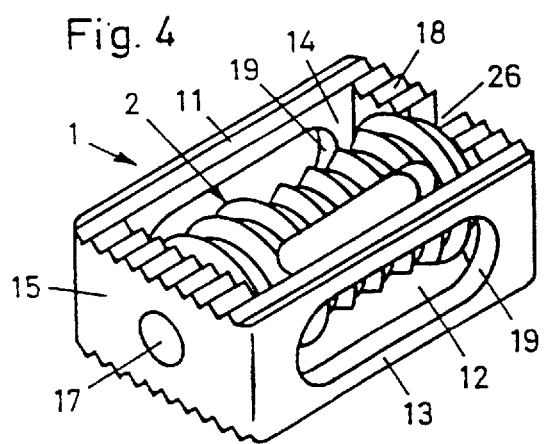

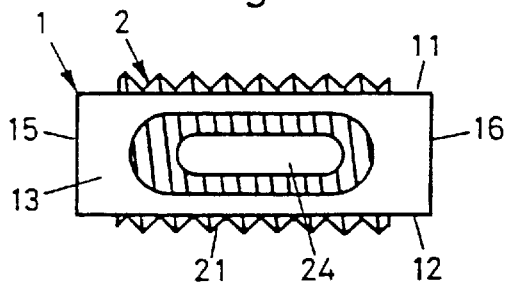
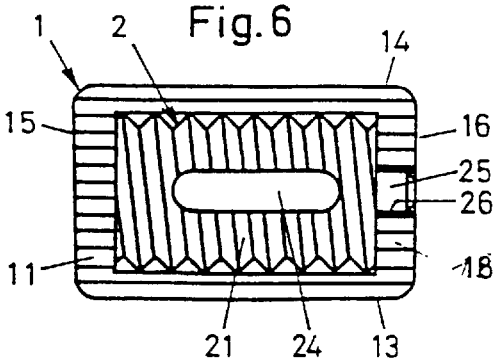
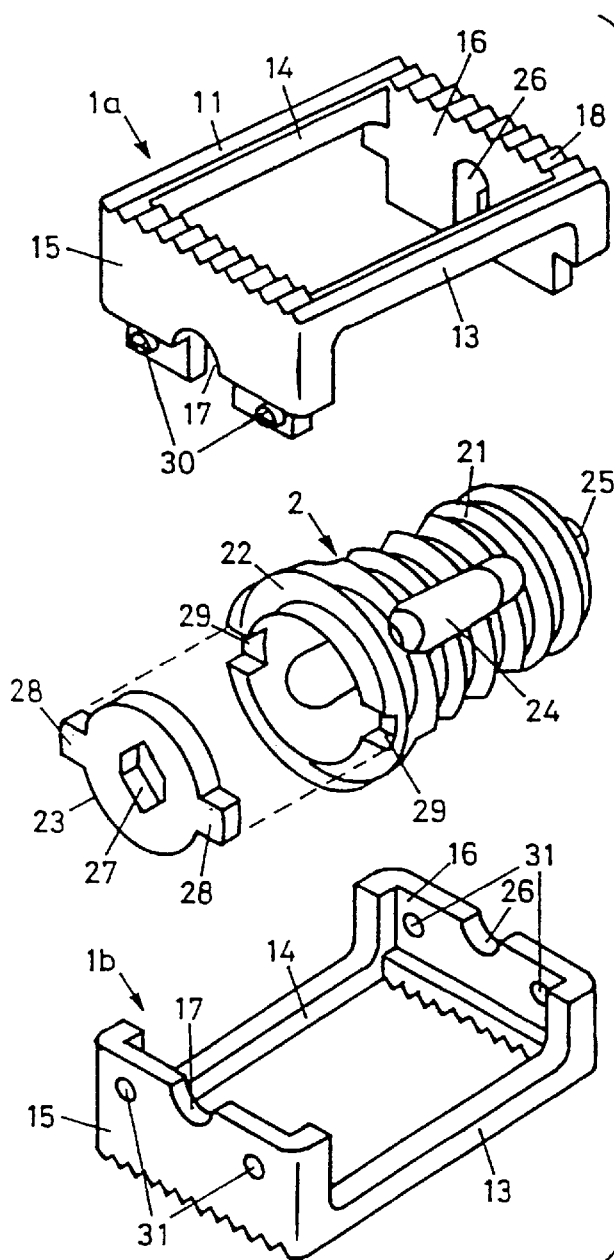
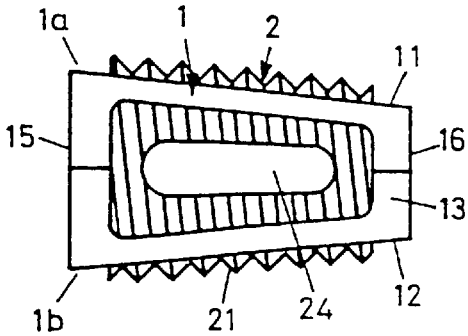

5,888,228

INTERVERTEBRAL IMPLANT WITH CAGE AND ROTATING ELEMENT

TECHNICAL FIELD

The invention relates to an intervertebral implant having a frame like cage which is open at its top and base faces with two lateral faces, a front wall and a rear wall. A rotating element is mounted in the cage so that the implant can be turned while being inserted into an intervertebral space.

BACKGROUND ART

Intervertebral implants are used for the fusion of vertebral bodies, especially in the area of the lumbar spine. One or two implants are used for each intervertebral space.

Various types of such intervertebral implants are already known from the prior art. However, these have the following disadvantages:

So that the implant can be inserted into the intervertebral region, the relevant vertebra must be distended with suitable instruments; and there is a risk that the implant will sink into the end plates of the affected vertebra.

SUMMARY OF THE INVENTION

The invention is intended to remedy these disadvantages. It is an object of the invention to create and intervertebral implant which can be turned into the cleared intervertebral space, if possible without distending instruments, in a controllable fashion, and with a minimum application of force.

This object is achieved through the use of an intervertebral implant having a frame like cage which is open at its top and base faces with two lateral faces, a front wall and a rear wall. A rotation element is rotatably mounted in the cage, and the outer surface of the rotation element has a helical structure which extends out of the cage beyond the cover and base faces. The front wall has an aperture so that a drive tool can be introduced so that the rotation element can be rotated to turn the implant.

It is thus possible to achieve the advantage that a minimum application of force is sufficient for the implantation, and that the implant can be inserted in a controlled fashion by means of the helical structure of the outer surface of the rotation element. The latter extends out of the cage beyond the cover and base faces. It is thus possible to use a minimally invasive and open surgical technique.

The cage-like frame structure with its large contact surface prevents the implant from sinking into the end plates.

The helical structure of the rotation element, which protrudes beyond the cage, makes it possible to turn the implant while it is being inserted, and to screw it into the intervertebral space.

A preferred further development consists in the feature that the rotation element of the implant is designed hollow and has a sealing cover on its front face. Bone chips or bone replacement materials thus can easily be filled into the rotation element, and the implant can be securely mounted with little manipulation. In this case, the cage is suitably designed so that it is assembled from two parts, to facilitate mounting. With this type of application, the rotation element preferably also has perforations in the form of longitudinal grooves, and the lateral surfaces of the cage have longitudinal hole recesses, so as to facilitate ingrowth of the bone.

The longitudinal grooves make it possible to check the ingrowth of the bone radiologically. The longitudinal recesses preferably have a cutting edge, which allows the end plate chips to penetrate into the hollow rotation body.

The cage can have the shape of a rectangular parallelepiped, with a rotation body in the shape of a circular cylinder, or it can be wedge-shaped with a correspondingly conical rotation body.

To increase the positional stability of the implant and the rotational stability of the adjoining vertebrae, the cover and base surfaces of the cage suitably have a three-dimensional structure, preferably in the form of longitudinal grooves.

The inventive implant has the following further advantages over the prior art:

secure against slipping;

improved x-ray transparency; and compressibility of bone material that may have been introduced into the rotation element.

BRIEF DESCRIPTION OF THE DRAWINGS

The invention and further developments of the invention will be explained in more detail below, by means of the partially schematic representation of an embodiment.

FIG. 1 shows a view, in perspective, of the cage of the inventive implant.

FIG. 2 shows a view, in perspective, of the open rotation element of the inventive implant.

FIG. 3 shows a view, in perspective, of the closed rotation element of the inventive implant.

FIG. 4 shows a view, in perspective, of the completely mounted, inventive implant.

FIG. 5 shows a side view of the implant of FIG. 4.

FIG. 6 shows a top view of the implant of FIG. 4.

FIG. 7 shows a view, in perspective, of another embodiment of the inventive implant in disassembled condition.

FIG. 8 shows a side view of the implant of FIG. 7 in its mounted condition.

DETAILED DESCRIPTION OF THE PREFERRED EMBODIMENTS

FIGS. 1–3 show the intervertebral implant in its disassembled condition. The implant consists essentially of a frame-like cage 11, open on its cover surface 1 and on its base face 12. It has two lateral surfaces 13 and 14, each of which has a longitudinal hole 19. The implant further has a front wall 15 with an aperture 17, and a rear wall 16. In this embodiment, the shape of the cage 1 is that of a rectangular parallelepiped. However, as shown in FIGS. 7 and 8, it can also have a wedge-like shape. The cage 1 can be designed either integral, as shown in FIG. 1, or also as composed of several parts, preferably two parts, as shown in FIGS. 7 and 8.

The cover and base faces 11, 12 have a three-dimensional structure 18, preferably in the form of longitudinal grooves, and this improves the insertion of the implant and the rotational stability of the adjoining vertebral bodies.

A hollow, circular-cylindrical rotation element 2 is rotatably mounted in the cage 1. For this purpose, the rear base face of the rotation element 2 has a journal 25, which can be inserted into the recess 26 in the rear wall 16 of the cage 1. The outer surface of the rotation element 2 has a helical structure 21 in the form of an outside thread, with a pitch of at least 2 mm and a depth of 0.8–2.2 mm, preferably 1.5–2.0 mm.

The length of the rotation element 2 is matched to the inside dimensions of the cage in such a way that it can be inserted into the cage snugly from above. In this way, it is enclosed in the cage with a rotatable mounting without further holding means (FIGS. 4 and 6). The front face 22 of the rotation element 2 has a detachable sealing cover 23 with a hexagonal aperture 27, which is used to receive a drive tool, so that bone chips or bone replacement material can be filled in. The sealing cover 23 has at least two mutually opposite cams 28, which latch into the corresponding grooves 29 on the front face 22 of the rotation element 2, so that the sealing cover 23 can be lowered flush in the front face 22. The rotation element 2 furthermore has perforations 24, which preferably are formed as longitudinal recesses with a cutting edge. The cutting edge preferably is undercut.

The front face 15 of the cage 1—as can be seen in FIG. 4—has an aperture 17 to introduce an instrument into the hexagonal aperture 27 of the sealing cover 23, so that the rotation element 2 can be rotated in the cage 1.

As FIG. 5 shows, the helical structure 21 in the form of an outside thread on the outer surface of the rotation element 2 protrudes 1.0 to 2.0 mm out of the cage 1 beyond the cover and face faces 11, 12.

FIGS. 7 and 8 show another embodiment of the inventive implant, in which the cage 1 is composed of two parts and the rotation element 2 is designed as a truncated cone. The design of the implant is largely identical with the design of the embodiment of FIGS. 1–6, except for the cage 1, which consists of two individual parts, a top part 1a and a bottom part 1b. The top part 1a has four cams 30, which latch into the corresponding four recesses 31 in the bottom part 1b, so that the rotation element 2, with its shape of a truncated cone, can be mounted easily and quickly between the two individual parts 1a, 1b, and can be fixed rotatably.

The cage 1 and the rotation element 2 preferably are made of titanium, titanium alloy, ceramic, or a biocompatible plastic.

The clinical application is described in detail below, in terms of the implant of FIGS. 7 and 8.

The hollow rotation element 2 shown in FIG. 7 is filled with bone chips (bone graft or bone replacement material) —possibly with compression—and is sealed with the sealing cover 23. Then the filled rotation element 2 is placed between the two individual parts 1a and 1b of the cage 1, such that the journal 25 of the rotation element 2 comes to lie in the recesses 26 of the individual parts 1a, 1b. By exerting a slight pressure from the top and bottom, the two individual parts 1a and 1b are closed to form the cage 1, which causes the cams 30 to latch in the recesses 31. The implant is now turned into the cleared intervertebral space, if possible without distending instruments. A drive tool— preferably a hexagon screwdriver—now can be inserted through the aperture 17 in the front face 13 of the cage 1 into the hexagonal aperture 27 of the sealing cover 23. In this way, the rotation element 2 can be turned easily in the cage 1. Due to its helical structure 21, which is in the form of a thread and which protrudes beyond the cage 1, it can also be screwed easily into the intervertebral space.

What is claimed is:

1. An intervertebral implant comprising a frame-like cage having open cover and base faces, two lateral faces, and front and rear walls, a rotation element rotatably mounted in the cage and having a helical structure on an outer surface; wherein the helical structure extends out of the cage beyond the cover and base faces; and the front wall has an aperture for receiving a drive tool for rotating the rotation element in the cage.

2. The implant of claim 1, wherein the rotation element is hollow and includes a sealing cover.

3. The implant of claim 1, wherein the cage has rectangular parallelepiped shape and the rotation element has a circular cylindrical shape.

4. The implant of claim 1, wherein the cage has a wedgeshape and the rotation element has a conical shape.

5. The implant of claim 1, wherein the rotation element includes perforations in the form of longitudinal recesses having cutting edges.

6. The implant of claim 1, wherein the cage has two parts.

7. The implant of claim 1, wherein the cover and base faces are equipped with longitudinal grooves.

8. The implant of claim 1, wherein the lateral faces are equipped with longitudinal hole recesses.

9. The implant of claim 1, wherein the helical structure comprises an outside thread or a helical groove or channel.

10. The implant of claim 1, wherein the helical structure extends out of the cage and beyond the cover and base faces, by 1–2 mm.

11. The implant of claim 1, wherein the pitch of the helical structure is at least 2 mm.

12. The implant of claim 1, wherein the depth of the helical structure is between 0.8 and 2.2 mm.

* * * * *